(12) United States Patent
Petursson et al.

(10) Patent No.: US 11,953,076 B2
(45) Date of Patent: Apr. 9, 2024

(54) INTERCHANGEABLE ATTACHMENT DEVICE

(71) Applicant: Ossur Iceland ehf, Reykjavik (IS)

(72) Inventors: Valgeir Petursson, Reykjavik (IS); Halldor Albertsson, Reykjavik (IS)

(73) Assignee: Ossur Iceland ehf, Reykjavik (IS)

( * ) Notice: Subject to any disclaimer, the term of this patent is extended or adjusted under 35 U.S.C. 154(b) by 0 days.

(21) Appl. No.: 17/717,329

(22) Filed: Apr. 11, 2022

(65) Prior Publication Data

US 2022/0235847 A1 Jul. 28, 2022

Related U.S. Application Data

(63) Continuation of application No. 16/797,353, filed on Feb. 21, 2020, now Pat. No. 11,333,219.

(60) Provisional application No. 62/862,444, filed on Jun. 17, 2019, provisional application No. 62/808,434, filed on Feb. 21, 2019.

(51) Int. Cl.
*F16G 11/00* (2006.01)

(52) U.S. Cl.
CPC .................. *F16G 11/00* (2013.01)

(58) Field of Classification Search
CPC ......... F16G 11/00; A61F 5/01; A61F 5/0102; A61F 5/0118; A61F 5/0123; A61F 5/0109; Y10T 24/2708
See application file for complete search history.

(56) References Cited

U.S. PATENT DOCUMENTS

| | | | |
|---|---|---|---|
| 793,325 A | 6/1905 | Stiles | |
| 1,402,594 A | 1/1922 | Gedney | |
| 1,469,281 A | 10/1923 | Stevens | |
| 2,021,619 A | 11/1935 | Waters et al. | |
| 3,139,662 A | 7/1964 | Barton | |
| 3,543,977 A * | 12/1970 | Lockridge | A45F 5/00 248/444 |
| 4,074,397 A | 2/1978 | Rosin | |
| D270,779 S | 10/1983 | Steinberg | |
| 4,441,490 A | 4/1984 | Nirschl | |
| 4,555,244 A | 11/1985 | Buell | |
| 4,586,499 A | 5/1986 | Kaletzky | |
| 4,727,865 A | 3/1988 | Hill-Byrne | |
| 4,831,997 A | 5/1989 | Greene | |
| 4,960,114 A * | 10/1990 | Dale | A61F 5/05866 602/21 |
| D330,505 S * | 10/1992 | Doyle | D8/356 |
| 5,669,901 A * | 9/1997 | LaFortune | A61F 13/64 24/306 |
| 5,921,949 A * | 7/1999 | Dray | A61F 5/0118 2/170 |
| 6,024,715 A | 2/2000 | Maxwell | |
| 6,186,969 B1 * | 2/2001 | Bell | A61F 5/0118 602/64 |

(Continued)

*Primary Examiner* — Robert Sandy
*Assistant Examiner* — Louis A Mercado
(74) *Attorney, Agent, or Firm* — Workman Nydegger

(57) ABSTRACT

An interchangeable attachment device includes a first attachment interface supporting a first component, and a second attachment interface supporting at least one second component. The first and second attachment interfaces define cooperating attachment portions arranged for securing an end portion of the first attachment interface to an end portion of the second attachment interface to form an attachment junction.

16 Claims, 6 Drawing Sheets

(56) References Cited

U.S. PATENT DOCUMENTS

| | | | |
|---|---|---|---|
| 6,561,994 B1 * | 5/2003 | Mills | A61F 5/0118 602/20 |
| 8,277,401 B2 | 10/2012 | Hammerslag et al. | |
| 8,458,864 B1 | 6/2013 | Patton et al. | |
| 9,839,548 B2 | 12/2017 | Ingvarsson et al. | |
| D843,103 S * | 3/2019 | Desaever | D2/978 |
| 11,304,838 B2 * | 4/2022 | Sigurdsson | A61F 5/0109 |
| 2002/0073516 A1 | 6/2002 | Behar | |
| 2007/0124899 A1 | 6/2007 | Israel et al. | |
| 2008/0065039 A1 | 3/2008 | Labit et al. | |
| 2008/0066272 A1 | 3/2008 | Hammerslag et al. | |
| 2009/0012438 A1 | 1/2009 | Frangi | |
| 2014/0123440 A1 | 5/2014 | Capra et al. | |
| 2017/0348131 A1 | 12/2017 | Petursson et al. | |
| 2018/0116852 A1 * | 5/2018 | Petursson | A61F 5/0109 |
| 2019/0105188 A1 | 4/2019 | Petursson et al. | |
| 2022/0202604 A1 * | 6/2022 | Sigurdsson | A61F 5/0106 |

\* cited by examiner

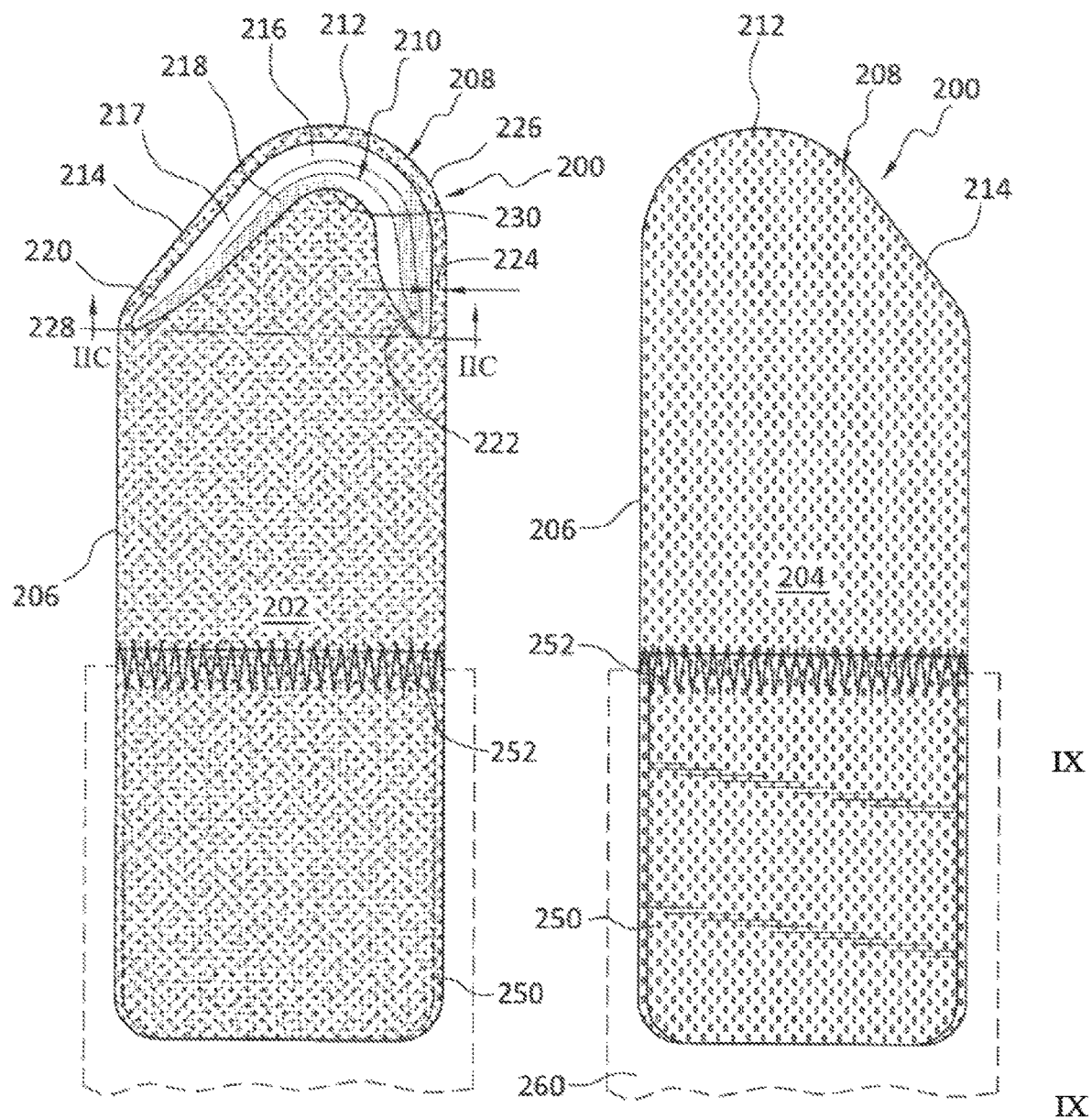
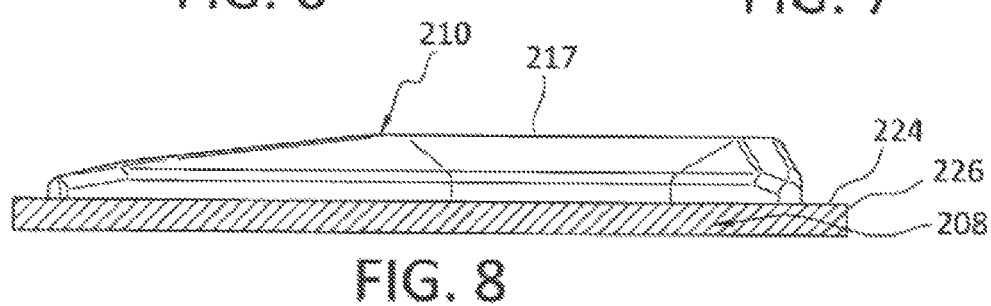
FIG. 6  FIG. 7
FIG. 8

INTERCHANGEABLE ATTACHMENT DEVICE

BACKGROUND

Attachment components and systems are used extensively in different devices and secure different components in desired configurations. An attachment system may attach or secure a first component, such as a cable, to a second component, such as a strap. In this and other scenarios, an attachment system is desired to provide robust and reliable support and attachment between the components.

Existing attachment systems may be complex, bulky, costly to manufacture, and/or difficult to use. These issues are especially evident in the fields of orthopedic, prosthetic, and medical devices, where proper functioning of different components across many unique and individual dimensions and needs is essential. The cost and complexity of manufacturing is compounded by the need to properly provide and/or match corresponding attachment interfaces between different components. Attachment systems must also be intuitive to use to ensure proper/compliant use, particularly in orthopedic, prosthetic, and medical device contexts.

It may be desired to connect a cable to a strap, such as in a tensionable dynamic force strap in an orthopedic brace, in which a cable attaches to a tensioning device such as a dial-tensioner to apply tension in the dynamic force strap to provide the desired level of forces or immobilization on a portion of the user's anatomy. The cable may attach or route to a cable attachment interface on or cooperating with a strap, such as a device having a channel arranged to receive the cable, but the cable interface may not be compatible with certain strap interfaces and accordingly may be difficult to properly attach to a strap. Such a scenario increases the complexity of manufacturing as specific strap interfaces must be provided to properly correspond to the cable interface to attach the cable to the strap.

The difficulty of properly matching different attachment interfaces is further compounded by the challenge of including desired features in the attachment interfaces. Dial-tensioning devices, elastic components, and other features may be needed at the attachment between components, which further adds to the cost and complexity of reliably and robustly attaching two components.

There is a need for an improved attachment system that overcomes the problem of existing attachment systems, being poorly adapted to match and attach between different components and thus requiring that component-specific attachment components are provided, which increases the costs of attaching two components, and reduces the likelihood of compliant use. There is also a need for an attachment device that overcomes the problem of attachment devices peeling away or otherwise being prone to accidental detachment from a strap or component to which they are attached.

SUMMARY

Embodiments of the interchangeable attachment device of the disclosure advantageously overcome the challenges of existing attachment systems that are difficult to properly match and attach by providing interchangeable component interfaces that are more simple, intuitive, and cost-effective to match, and provide reliable and robust attachment. The interchangeable attachment device of embodiments of the disclosure may generally include a first attachment interface supporting and/or attached to a first component and a second corresponding attachment interface supporting and/or attached to at least a second component. The advantage of the first and second attachment interfaces is that different components may be swapped or interchanged according to the desired first and second components, allowing a user or clinician to readily adapt the attachment system according to its particularities and/or a user's needs.

The first and second attachment interfaces may each comprise corresponding locking or attachment portions that robustly and reliably secure the interfaces to each other in an intuitive, predictable, and cost-effective way. The attachment interfaces may be arranged to attach at an attachment junction and may define features such that the attached first and second attachment interfaces define a smooth and/or substantially unitary structure in the attached state.

The attachment portions may comprise corresponding protruding and receiving portions defined by the corresponding attachment interfaces. A protruding portion according to embodiments may comprise an extending portion and an engagement part arranged to cooperate with a retention member on the receiving portion. A receiving portion according to embodiments may be arranged to receive the corresponding protruding portion to ensure a robust attachment and may facilitate a removable attachment by providing locking/unlocking elements.

A locking/unlocking element according to embodiments may be provided on the protruding portion and arranged to cooperate with a corresponding recess defined by the receiving portion, allowing a user or manufacturer to disengage the attached first and second attachment interfaces. A body portion of the attachment interface defining the receiving portion may define an aperture or other feature arranged to facilitate disengagement of the locking portion from the recess by a user.

The first attachment interface may support and cooperate with a cable, such as a cable in a dial-tensioning device. The second attachment interface may support or attach to straps, such as dynamic tensioning straps, frame components, additional cables, and/or any suitable component. The first attachment interface is not limited to cooperating with a cable, but rather may be configured with any component or feature for securing the second attachment interface to an object. It may comprise clips, clamps, teeth, D-rings, overmolded portions, adhesives, snaps or other fasteners, and/or other features known to the skilled person.

The second attachment interface may comprise an attachment or locking structure arranged to secure the second component, either releasably or non-releasably. In embodiments in which the second component is a strap, the attachment structure may comprise a locking structure for securing the straps to the second attachment interface, including but not limited to clips, clamps, teeth, D-rings, overmolded portions, adhesives, and/or other features.

The first and/or second attachment interface may support additional features arranged to cooperate with the first and/or second components, such as dial-tensioning devices. The first and/or second attachment interface may define features such as elastic segments that allow for flexibility and/or stretching between the first and second attachment interfaces. Embodiments of an attachment system comprising more than two attachment interfaces and/or components arranged for being interchangeably attached are also contemplated.

These and other features, aspects, and advantages of the present disclosure will become better understood regarding the following description, appended claims, and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an attachment system, and in no way limit the structures or configurations according to the present disclosure.

FIG. 6 is a front plan view of another embodiment of a strap attachment.

FIG. 7 is a rear plan of the strap attachment of FIG. 6.

FIG. 8 is a cross-sectional view taken along line IIC-IIC in FIG. 6.

DETAILED DESCRIPTION OF VARIOUS EMBODIMENTS

Figure 1:
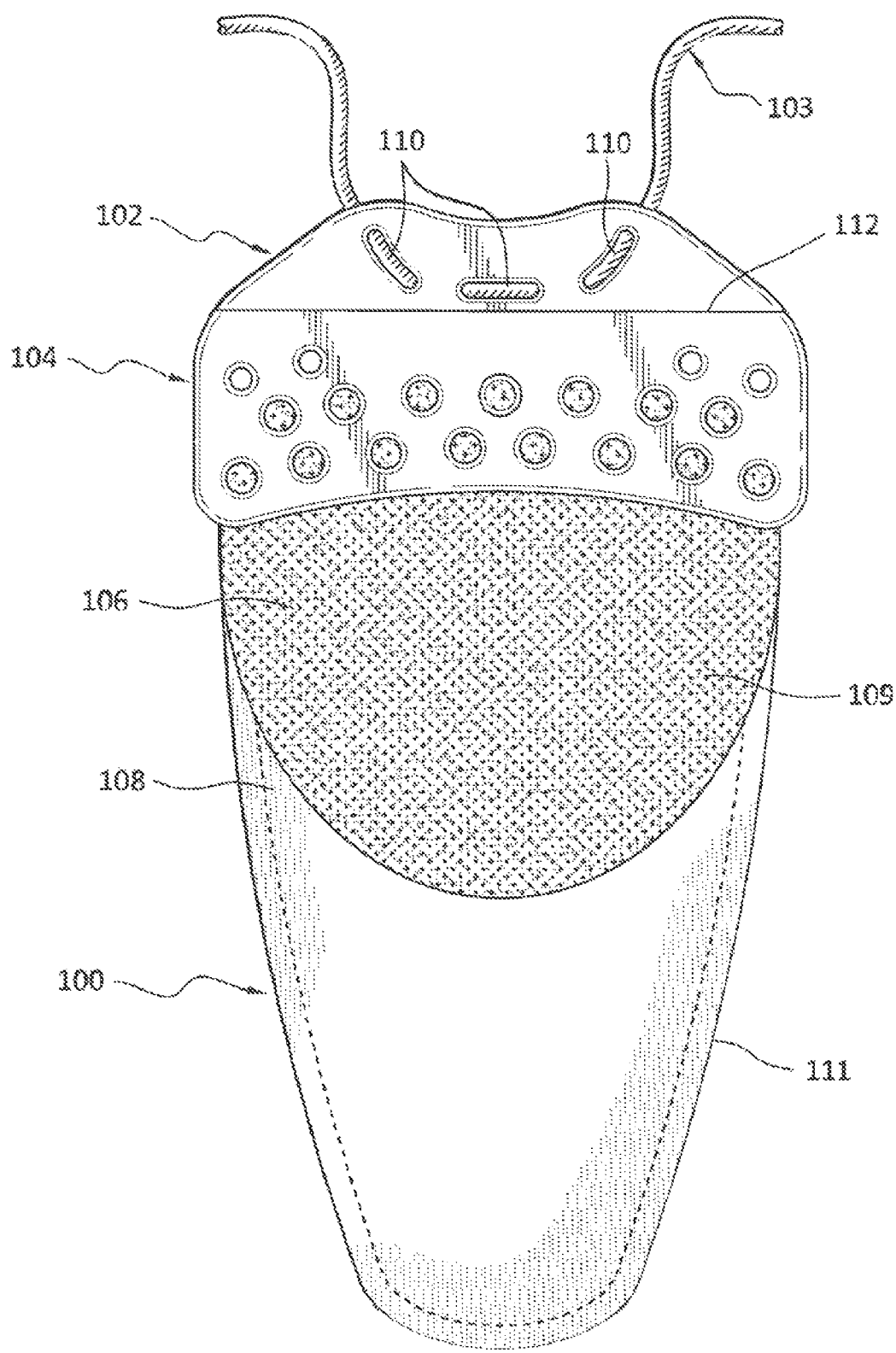
FIG. 1 shows an elevational view of an interchangeable attachment device according to an embodiment.

A better understanding of different embodiments of the disclosure may be had from the following description read with the accompanying drawings in which like reference characters refer to like elements. While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

The interchangeable attachment device embodiments of the present disclosure advantageously address the problem of existing attachment interfaces only being suitable for certain components, which increases the cost and complexity of providing or manufacturing devices and reduces compliant use. The problem is addressed by providing attachment interfaces of an interchangeable attachment device which are configured to attach to different components and provide a robust and reliable attachment therebetween.

FIG. 1 shows an elevational view of an interchangeable attachment device 100 according to an embodiment of the disclosure. The attachment device 100 may comprise a first attachment interface 102 and a second attachment interface 104 selectively securable to one another. By "selectively securable," the first attachment interface 102 can be removed at will from the second attachment interface 104. The first attachment interface 102 may be arranged as a cable interface supporting a cable such as a tensioning cable, as taught in U.S. Pat. No. 8,277,401, granted on Oct. 2, 2012, and incorporated herein by reference. The second attachment interface 104 may be arranged as a strapping interface supporting or connecting to a strap such as a dynamic force strap, although it will be understood that the first and second interfaces 102, 104, and the cables and straps connected thereto, are merely exemplary, and more and other suitable components may be provided in other embodiments of the disclosure.

An example of the strap interface may be found in at least U.S. Patent application publication no. 2019/0105188, published on Apr. 11, 2019, which belongs to the applicant of the present disclosure and is incorporated herein by reference. In other embodiments, the interchangeable attachment device 100 may attach a cable to a strap using a mounting bracket that defines a cable channel for slidably receiving the cable through a thickness of the bracket, and allowing the strap to be tensioned by the cable, as described in U.S. Patent application publication no. 2017/0348131, published on Dec. 7, 2017, which belongs to the applicant of the present disclosure and is incorporated herein by reference. The depiction of a connection between a cable as a first component and a strap as a second component is merely exemplary, and any type or number of components may be joined using embodiments of the interchangeable attachment device 100 according to the disclosure.

The interchangeable attachment device 100 advantageously may facilitate a robust and reliable attachment between the first and second interfaces 102, 104, and by consequence between the components supported by the first and second interfaces 102, 104. In the depicted embodiment, the first and second interfaces 102, 104 are joined at an attachment junction 112, which may be arranged to facilitate a robust and snug engagement between the first and second interfaces 102, 104 such that the interchangeable attachment device 100 defines a substantially unitary body or structure. As shown in FIG. 1, the first and second interfaces 102, 104 are generally coextensive relative to one another at the attachment junction 112.

The first and second interfaces 102, 104 may be arranged to be interchangeable, such that attachment interfaces may be easily and cost-effectively swapped, substituted, or replaced as necessary. In the context of an orthopedic brace, a strap may need to attach to a cable of a dial-tensioning element. However, existing dial-tensioner-compatible attachments may require that the strap attachment is specially configured to accommodate the existing dial-tensioner and/or cable attachments.

By providing an interchangeable attachment device 100 comprising first and second interchangeable attachment interfaces 102, 104 according to embodiments of the disclosure, the cable may be simply and reliably attached to the strap without providing numerous and/or specialized quantities of attachment components each of which is necessarily specific to a different component. Manufacturing costs and complexities are reduced, as the number and complexity of attachment systems that must be provided and/or stocked as part of the manufacturing process are substantially reduced. Compliant use is also increased, as the intuitiveness of use of a reduced number of attachment interface types is increased relative to existing attachment devices.

Figure 2:
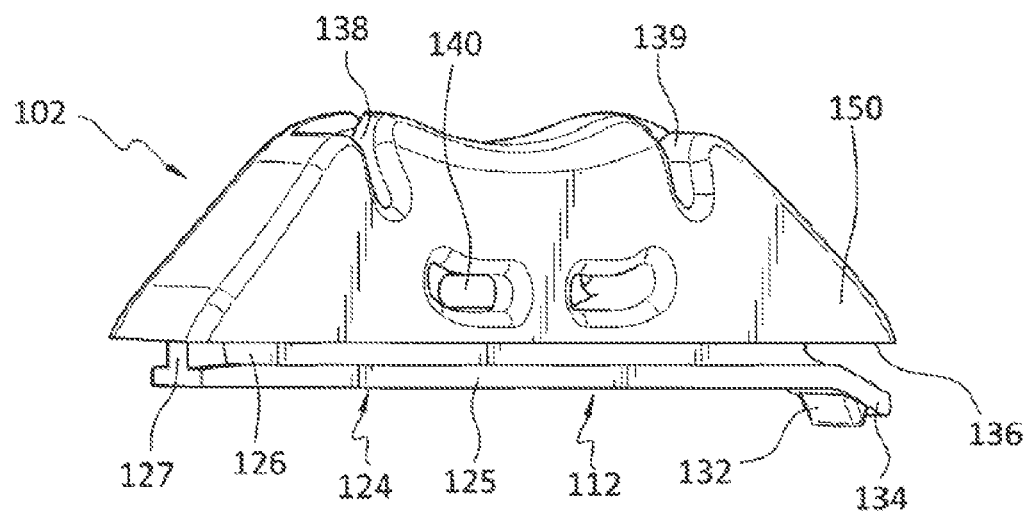
FIG. 2 shows a side perspective view of a cable attachment portion according to the attachment system of FIG. 1.
Figure 3:
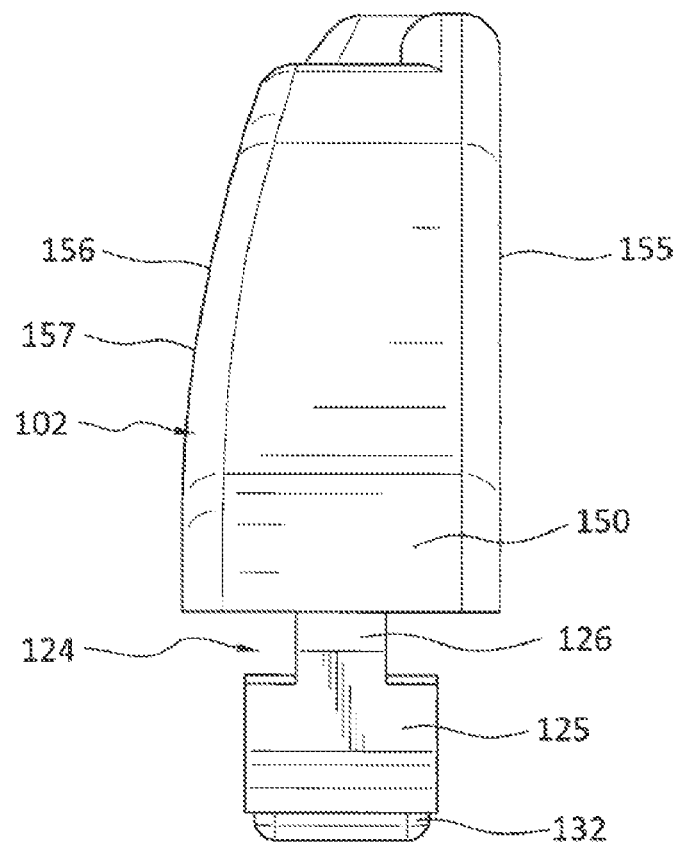
FIG. 3 shows a side view of the cable attachment portion of FIG. 2.

As seen in FIGS. 2-3, in embodiments in which the first interface 102 is arranged as a cable interface to attach a cable 103, the cable interface 102 may comprise a body 150 defining through a thickness of the body 150 a channel 138 accessible through apertures 139. The channel 138 may allow for sliding translation of the cable 103 therethrough, which may allow for greater flexibility and ease of use. A first component supported by the cable interface 102 may be a cable 103, such as a cable utilized by a dial-tensioning device, and may be arranged to pass through and secure to the first attachment interface 102 at or through the channel 138. The body 150 may further define a plurality of apertures 110, 140 extending a distance into or through the body 150. The plurality of apertures 110, 140 may correspond to and/or expose a portion of the channel 138 such that a corresponding portion of the cable is visible through the apertures 110, 140.

The cable 103 may be provided with indicia that a user may view through the plurality of apertures 110, 140 for ascertaining the desired level of tension or fit. The plurality of apertures 110, 140 may also advantageously reduce bulk, weight, and therefore cost of the first attachment interface 102. The first attachment interface 102 may have distinct first and second sides 155, 156, with a different plurality and pattern of apertures corresponding to each side. For instance, the first plurality of apertures 110 located on the first side 155 may have a different pattern than a second plurality of apertures 140 located on the second side 156 opposite the first plurality of apertures 140. In embodiments, the first attachment interface 102 may be arranged to lock the cable in place and not to allow sliding translation or adjustment of the cable through the channel 138.

The cable 103 may be formed of any suitable material, including metal, alloys of metals, polymer, fiber-filled polymers, combinations thereof, or any other suitable material. The cable 103 may be formed of materials allowing the cable 103 to flexibly extend from and within the first attachment interface 102. In embodiments, the cable 103 is formed from a different material than the material forming the first attachment interface 102.

The first attachment interface 102 may be provided with a locking element, provided in the depicted embodiment as a protruding portion 124, arranged to correspond and attach to a corresponding locking element, formed in the depicted embodiment as a receiving portion 122, on the second attachment interface 104. The protruding portion 124 may be elongate and extending generally along a width of the first attachment interface 102. The protruding portion 124 may comprise an extension part 126 extending from the body 150 towards the second attachment interface 104 and supporting an engagement part 125. The engagement part 125 may form a lip or an edge that extends along substantially an entirety of the protruding portion 124 and may be arranged to slidably engage a corresponding lip or edge on the corresponding receiving portion 122. In embodiments, the engagement part 125 may be bifurcated by and extend along opposed sides of the extension part 126. The depiction of complementary protruding and receiving portions 124, 122 is merely exemplary, and any suitable connection mechanism may be used and is contemplated by the disclosure.

The protruding portion 124 and the engagement part 125 may be bounded by a stop-engaging surface 127 on a first end of the protruding portion 124 and by an engagement stop 134 at a second, opposed end of the protruding portion 124. The stop-engaging surface 127 and the engagement stop 134 may be arranged to cooperate with a corresponding receiving portion 122, as described in greater detail below.

Alternative arrangements of the protruding portion 124 are envisioned. The arrangement of the engagement part 125 relative to the extension part 126 need not be symmetric and need not be centered relative to the body 150 of the first attachment interface 102. Any suitable locking portion arranged to attach to a corresponding locking portion may be used and is contemplated by the disclosure.

As discussed, the first attachment interface 102 may define distinct first and second sides 155, 156 between the first and opposed ends. The first side 155 may have a substantially flat surface, while the second side 156 may define a curved surface defining a profile 157. One of the first and second sides 155, 156 may be arranged as a cosmetic or upward-facing side, while the opposite side may be arranged to lay flat against an article or component underneath the opposite side. In certain embodiments, the first side 155 may be arranged to lay flat against components underneath it, such as against the frame or body of an orthopedic or prosthetic device. This arrangement advantageously reduces bulk and complications of use. The second side 156 may define an aesthetically pleasing and easy-to-grip surface, including frictional or grip-enhancing features or indicia, to face upwards and to be engaged by a user.

The first attachment interface 102 may be formed of any suitable material, including metal, polymer material including thermoset and thermoplastic materials, generally as plastic materials, fiber-filled polymers such as carbon fiber, combinations thereof or otherwise. The first and second attachment interfaces 102, 104 may be formed from rigid or semi-rigid materials, and more specifically from materials different from the first and second components.

In embodiments, the protruding portion and engagement portion 124, 125, and regions defining the channel 138 may be formed of structurally sound material for ensuring a robust and reliable attachment, while other regions may be formed of lightweight and/or resilient material. The entire attachment interface 102 may be formed of a lightweight and/or resilient material. It will be understood that the described embodiments are merely exemplary, and other arrangements, shapes, and structures are contemplated within the disclosure.

Figure 4:
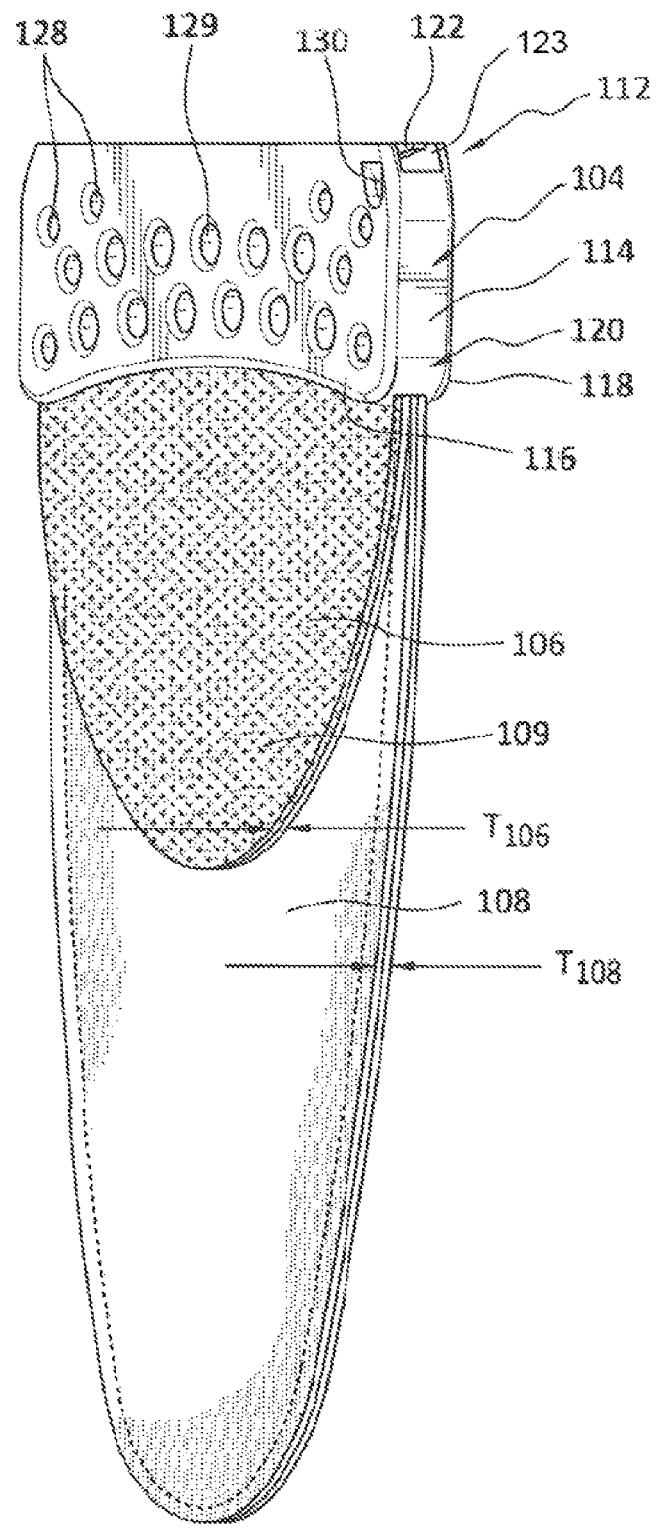
FIG. 4 shows a side perspective view of a strap attachment portion according to the interchangeable attachment device of FIG. 1.
Figure 5:
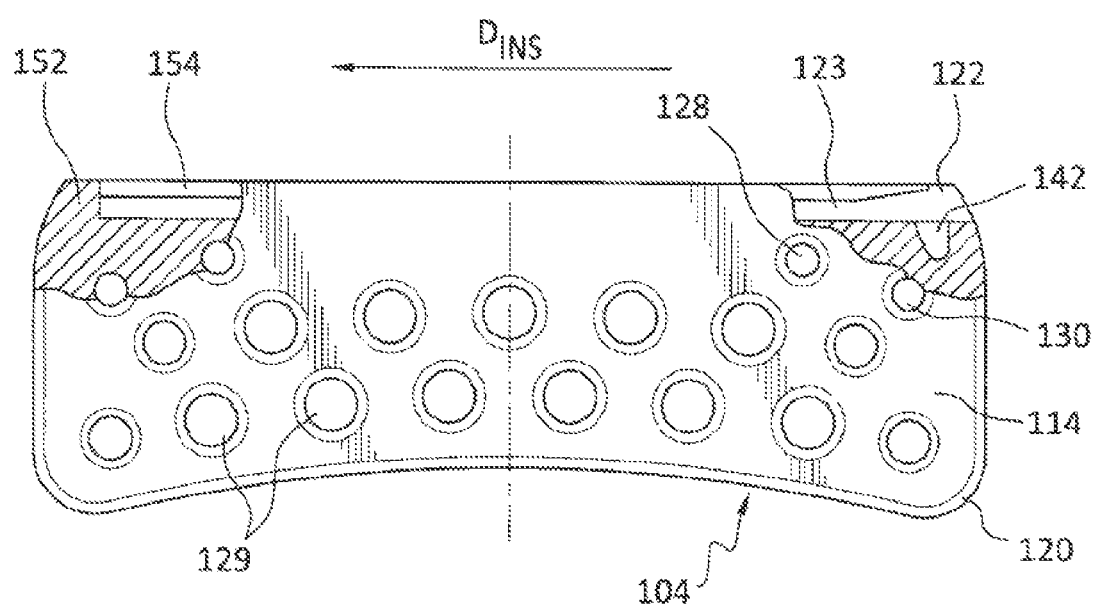
FIG. 5 shows a partial cutaway view of a strap attachment interface according to the strap attachment portion of FIG. 4.
Figure 9:
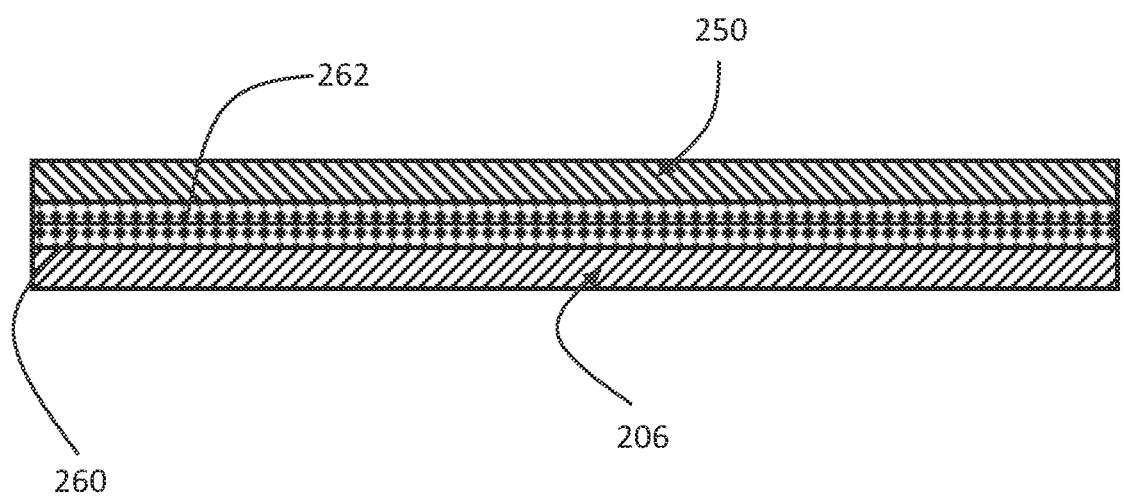
FIG. 9 is a cross-sectional view taken along line IX-IX in FIG. 7.

As seen in FIGS. 4 and 5, a second attachment interface 104 may be arranged to correspond to and attach to the first attachment interface 102 with a reliable and robust attachment and in a simple, intuitive manner. The second attachment interface 102 may also be arranged to support or connect to a second component. The first and second components may thereby be connected to each other. In certain embodiments, the second component may be formed as one or more straps 106, 108. In embodiments in which the first component is a cable and the second component is the one or more straps 106, 108, a more reliable, robust, simple, and intuitive attachment between a cable, such as a tensioning cable, and straps, such as dynamic force straps, may be provided compared to existing component-specific attachment devices, as the interchangeability of attachment interfaces according to embodiments of the disclosure simplifies the provision of matching attachment portions.

The second attachment interface 104 may be arranged to attach to the first attachment interface 102 at the attachment junction 112 by defining a receiving portion 122 corresponding to the protruding portion 124 that is defined by the first attachment interface 102. In an embodiment, the receiving portion 122 may be defined in a body 114 of the second attachment interface 104 such that when the first and second attachment interfaces 102, 104 are attached, the interchangeable attachment device 100 defines a smooth and substantially unitary structure. The second attachment interface 104 may comprise first and second sides 116, 118 corresponding to the first and second sides 155, 156 of the first attachment interface 102.

In embodiments, the first attachment interface 102 may define portions or shoulders 136 at appropriate portions of the body 150, for example at an end portion of the body 150. The shoulders 136 may be arranged to abut a corresponding portion of an end portion or the top-most surface of the body 114 of the second attachment interface 104 in the attached configuration such that the interchangeable attachment device 100 comprises a smooth, continuous, and substantially unitary structure with no or substantially no gaps defined between the abutting surfaces of the end portions of the first and second attachment interfaces 102, 104.

The receiving portion 122 may comprise a receiving channel 123 extending through at least part of a thickness of the body 114 and defining an aperture 126 on a first side of the second attachment interface 104. The receiving channel 123 may be defined in part by a vertical channel 154 arranged to overlap, at least partially, an inserted protruding portion 124 of the first attachment interface 124. The vertical channel 154 may extend from a single side of the receiving channel 123 or may extend from both sides of the receiving channel 123 and may define a region (not shown) through which the extension part 126 may pass as the protruding portion 124 slidably engages the receiving portion 122.

The receiving channel 123 may be bounded at a second end opposite the aperture 126 by a terminal 152. The terminal 152 may be formed as a stop or a wall and may be arranged to engage the stop-engaging surface 127 defined by the protruding portion 124. The cooperation of or contact between the terminal 152 and the stop-engaging surface 127 indicates a complete insertion of the protruding portion 124 into the receiving portion 122 in an insertion direction Dins. At an opposed first end of the receiving channel 123, and proximate the aperture 126, a detent 142 may be formed for receiving the locking element 132. The detent 142 may be formed as a recess arranged to interengage the locking/unlocking element 132. In other embodiments, a locking/unlocking mechanism may be defined proximate the terminal 152, exterior to the channel 123, or within an interior portion of the channel 123.

In embodiments, the locking/unlocking element 132, which may extend downwardly from the protruding portion 124, may extend into and interengage the detent 142 to lock the first and second attachment interfaces 102, 104 in place relative to one another by preventing the protruding portion 124 from sliding out of the receiving portion 122 in a direction opposite the insertion direction DIns.

An aperture 130 may be defined in the body 114 and extends through at least a partial thickness of the body 114 to the detent 142. A user, manufacturer, or clinician may disengage the first and second attachment interfaces 102, 104 or to disconnect the components from each other, such as to interchange the interfaces 102, 104, by accessing the locking/unlocking element 132 via the aperture 130, such as with a tool inserted through the aperture 130. The aperture 130 may extend through an entire thickness of the body 114 or may be limited to a single side of the body 114, for example an upwardly or outwardly facing side. Other mechanisms or procedures for locking/unlocking the interfaces are likewise contemplated.

In embodiments, an engagement stop 134 may be provided at the end of the protruding portion opposite the stop-engaging surface 127. The engagement stop 134 may form an engagement or connection with an end portion of the receiving channel 123. In embodiments, the engagement stop 134 may be pre-tensioned in a direction such that the protruding portion 124 is biased against disengagement from the receiving portion. The engagement stop 134 may be pre-tensioned downwardly to tension the unlocking element 132 into the detent 142, thereby preventing unintentional disengagement of the first and second attachment components 102, 104.

The bias may increase friction between the protruding and receiving portions so as to resist unintentional disengagement. It will be understood that the described embodiments of the attachment components including the stop-engaging surface 127, receiving channel 123, terminal 152, unlocking element 132, detent 142, and the engagement stop 134, as with other elements of the disclosure, are merely exemplary and are not limiting. Additional mechanisms for attaching the interfaces 102, 104 are contemplated; for example, adhesive material may be applied to the junction 112 after the locking parts 124, 122 have been connected to ensure that the first and second attachment interfaces do not detach.

By providing corresponding protruding and receiving portions 124, 122, the first and second attachment interfaces 102, 104 may be interchanged as necessary to provide a reliable and robust attachment between any desired and/or suitable components, which may be matched and/or interchanged with greater ease. If a cable must be attached to a strap, the interchangeable attachment device 100 of the disclosure advantageously allows attachment interfaces 102, 104 to simply and intuitively connect the cables and straps without the necessity and burden of providing and/or matching specific attachments or terminals for each component. The interchangeable attachment device 100 is not limited to attaching via corresponding protruding and receiving portions, but rather may attach via any suitable attachment mechanism.

The interchangeable attachment device 100 may attach a first component, such as a cable, to a second component, such as a strap, using a unitary flexible tab that attaches to a strap, for example by hook-and-loop fastener or any other suitable fastener, and defines a cable guide through a thickness of the tab, allowing a cable to slidably engage the tab through the guide. Other attachment systems for facilitating the attachment of two components are likewise envisioned within the disclosure.

The second attachment interface 104 may comprise a locking or attachment portion 120 arranged to attach to or lock a second component, such as straps 106, 108. The locking portion 120 may be arranged to attach to any suitable component. In some embodiments, the locking portion 120 may be arranged for locking to straps; in others, the locking portion 120 may be arranged for attaching to a frame component; in others, the locking portion 120 may be arranged for attaching to a cable. The locking portion 120 may be arranged for attaching in any suitable manner to any suitable component and is not limited to the described embodiments.

In an embodiment, the locking portion 120 may be arranged to attach at end portions of the first and second straps 106, 108. The locking portion 120 may comprise an overmolded portion comprising for example a thermoplastic material arranged to grip or clamp the straps 106, 108. In certain embodiments, the overmolded portion may extend or penetrate a distance into the straps 106, 108, thereby non-removably attaching to the straps 106, 108. In other embodiments, the overmolded portion may be configured to removably attach to the straps 106, 108. The overmolded portion may comprise any suitable material, including polymeric materials, and may be arranged to be rigid or resilient. The straps may have fibers or protruding features (hook or loop material, collectively referred to herein as "hook-and-loop material") that interlock with material of the overmolded portion. In embodiments, the plastic material of the overmolded portion is different than a material forming the straps 106, 108 and is configured or chosen to interlock with the material forming the straps 106, 108, which may be formed of different material from each other.

By locking the first and second straps 106, 108 at the locking portion 120, the second attachment interface 104 can securely retain the first and second straps 106, 108 relative to the interface 104, with the first and second straps 106, 108 serving a suitable purpose in a device, such as dynamic force straps in an orthopedic device. Alternatively, the first and second straps 106, 108 may advantageously serve to engage with and attach to a component, for example a textile strap. The first and second straps 106, 108 may comprise hook-and-loop material on an inward-facing and/or outward-facing surface suitable for engaging and grasping the textile material of a distinct strap, thereby securely attaching the textile strap to the attachment interface 104 through the hook-and-loop attachment. In embodiments, the first and second straps 106, 108 are configured to extend over opposed surfaces of the textile strap to surround and securely retain the textile strap relative to the attachment interface 104.

By the term "overmolded," it is intended to represent a process where a single part is created using two or more different materials in combination. Typically the first material, sometimes referred to as the substrate, is partially or fully covered by subsequent materials (overmold materials) during the manufacturing process. The substrate can include: a machined metal part, a molded plastic part, a textile, or even an existing product like threaded inserts, screws, or electrical connectors. It is the substrate that becomes a single continuous part with the material molded over it and composed of chemically bonded and often mechanically interlocked materials of separate types.

A distinct structure, as in the "overmold," is created when an overmolding process is employed. Some examples include a first plastic overmolding a second plastic having different properties from the first plastic. A first rigid plastic substrate may be molded, and then another rigid plastic is molded over or around the substrate to provide a different property or color. In another example, a first rigid plastic substrate is molded, and then a soft rubber or thermoplastic elastomer is molded onto or around the substrate to provide a softer grip over the rigid part.

In typical processes of overmolding, the substrate material or part is placed into an injection molding tool, at which point the overmold material is shot into, onto, or around the substrate. When the overmold material cures or solidifies, the two materials become joined together as a single part. The substrate and overmold material interlock in some mechanical capacity. This way, the two materials will not only be bonded together chemically, they will also be held together physically.

In the instance of the straps, the textile or other material forming the straps may interlock with the second interface 104 material overmolding the straps. In yet other embodiments, the locking portion 120 may comprise D-rings configured for slidably engaging the straps 106, 108. The locking portion 120 may comprise teeth that extend a distance into and engage the straps 106, 108. In embodiments, the teeth may be arranged to disengage by providing a hinge portion.

The straps 106, 108 may comprise any suitable configuration and may define any suitable feature. In an embodiment, the straps 106, 108 may comprise fastener material 109 along a surface and anti-attachment material 111 along another surface. In the embodiment of FIG. 1, the fastener material 109 may be a hook-and-loop-type fastener. In an embodiment, the straps 106, 108 may be arranged with fastener material 109 on outwardly facing sides thereof (i.e. a side of each strap 106, 108 that faces away from the other strap) such that the straps 106, 108 do not lock to each other. The straps 106, 108 may be arranged to bend away from each other and from the second attachment interface 104 flexibly and may be arranged with different sizes and shapes, this enabling the straps 106, 108 to at least be suitable for use and cooperation with a variety of different components or devices. The straps 106, 108 may further comprise one or more layers which define a thickness T106, T108, which may be the same or a different thickness, and which may vary or be uniform over a length of the strap.

The second attachment interface 104 may be arranged in any suitable configuration. In an embodiment, the body 114 may extend a length sufficient to allow multiple components, such as straps, to be attached at the locking portion 120 side by side rather than in a stacked or layered arrangement. The locking portion 120 may additionally be arranged to face a different direction; the second component, such as the straps 106, 108, may be arranged to attach at the locking portion 120, or multiple locking portions, at different portions. The straps may connect to the second attachment interface 120 at right angles from one another, for example at a T-shaped junction. The locking portion or portions 120 may face away from the receiving portion 122 in any suitable angle or shape, and the interchangeable attachment device 100 is not limited to the embodiments discussed but can take any suitable configuration.

In an embodiment, the locking portion 120 may be interchangeable on the second attachment interface 104. The locking portion 120 may define a protruding and/or receiving portion arranged to cooperate with a corresponding locking or receiving portion on the second attachment interface 104 as described in relation to the interfaces 102, 104. This advantageously allows different components, such as straps, to be attached to a single attachment interface 104 without defining or reconfiguring multiple types of interfaces.

The body 114 of the second attachment interface 104 may define a plurality of apertures through at least a thickness of the body 114. Certain of the apertures 129 may be arranged to extend a distance to show a portion of the second component, such as the straps 106, 108. The straps 106, 108 may comprise indicia arranged to be visible through the apertures 129, enabling proper attachment of the straps 106, 108 by the locking portion 120 and confirmation of proper attachment. Other apertures 128 may extend continuously through an entirety of the body 114. The apertures 128 may be arranged to extend closer to an end portion of the interface 104 while the apertures 129 may be arranged to extend closer to the strap portions 106, 108. The apertures 128 may advantageously reduce a weight and cost of the interchangeable attachment device 100, or may define a better grip, or may improve aesthetics, and/or may additionally allow a user to ascertain that the straps 106, 108 have not been inserted into the body 114 too far.

The interchangeable attachment device 100 may further define additional features and components. Some of the additional features may be arranged for facilitating the simplicity, intuitiveness, reliability, and robustness of the attachment between attachment interfaces. In an embodiment, the first and/or the second attachment interface 102, 104 may define within a portion thereof an elastic segment. The elastic segment may be arranged to provide flexibility and/or elasticity when the components are in the attached configuration or being attached. In an embodiment, the elastic segment may provide an easier attachment by allowing a user or manufacturer to more easily align the locking parts, for example, by bending one or more interfaces as needed, for inserting the protruding portion 124 or for disengaging the interfaces using the locking/unlocking mechanism.

In other embodiments, the first and/or second attachment interfaces 102, 104 may support features such as adjustment features. In the embodiment of FIG. 1 in which the first attachment interface 102 is arranged to cooperate with a cable of a dial-tensioning device, the first attachment interface 102 may support and cooperate with a dial tensioner to cooperate with and adjust a length of the cable. In embodiments where the second attachment interface 104 is arranged to cooperate with one or more straps 106, 108, the second attachment interface 104 may define an adjustment feature to adjust a length or tension in the straps 106, 108.

FIGS. 6-8 illustrate an alligator attachment 200 arranged for extending a strap or providing an engaging portion for securing to a surface of a sleeve, opposing strap or other surface adapted for receiving the attachment 200. The attachment 200 includes a first surface 202 having a first texture or functional surface, and a second surface 204 having a second texture or functional surface. For example, the first surface 202 may be a brushed or unbroken loop material or a textile material, whereas the second surface 204 may be hook material for coupling to a unbroken loop material. Other fastening means may be contemplated and the disclosure is not limited to hook material.

The attachment 200 has a strip or elongate section 206 and a head section 208, with a flap 250 connected to the elongate section 206. The attachment 200 is arranged to secure to a strap 260 with a cooperating surface in which at least the first surface 202 interlocks, as in hook and loop. As shown, the first surface 202 extends along an entirety of the elongate and head sections 206, 208, and the second surface 204 extends along an entirety of the elongate and head sections 206. Alternatively, the first and second surfaces 202, 204 may be arranged in segments in that they are arranged short of the entire length or width of the first and second surfaces 202, 204.

The flap 250 may be secured along any point of the elongate section 206. In the illustrated embodiment, the flap 250 is generally stitched or otherwise secured to the elongate section 206 mid-height from the head section 208 at a junction 252. It is preferred that the flap 250 is secured below the head section 208, as it is generally cut or formed to extend parallel to elongate section 206. While the flap 250 may have a preferred width matching the width of the elongate section 206, it may likewise be formed wider or narrower than the width of the flap 250 depending on the width of the strap 260 upon which the attachment 200 is secured. An inner surface of the flap 250, not shown, may be arranged similarly as the inner or first surface 202 of the elongate section 206. The elongate section 206 and the flap 250 define hook elements 261, 262 on opposite surfaces to one another from the junction 252 to the second end of the attachment device 200.

A traction element 210 may be provided along the head section 208. The head section 208 has a profile forming a tip 212 and a sloped edge 214. The traction element 210 corresponds to the profile of the head section 208 with first and second ends 220, 222 on opposed sides of the head section 208, generally along a line 228 separating the head section 208 from the elongate section 206. The traction element 210 is spaced away by a distance 224 from a profile or peripheral edge 226 of the head section 208.

While the elongate section 206 and the head section 208 may be continuous with one another and have a substantially flexible configuration in that they conform to a shape in which they bend, the traction element 210 is preferably rigid or semi-rigid in comparison to the elongate section 206. As shown, a same material may extend across continuously without interruption across the first and second surfaces 202, 204 of the attachment 200, across both the elongate and head sections 206, 208. Alternatively, different materials may define the first and second surfaces 202, 204 at designated locations, either offering different fastening properties or used to inhibit or increase flexibility at such designated locations.

The traction element 210 is arranged to offer a raised profile 217 protruding outwardly from the head section 208 to better enable a user to grasp the attachment 200. In addition to the raised profile 217, the traction element 210 may have additional ergonomic features with first and second slopes 216, 218 leading to the raised profile 217. The raised profile 217 may form a depression 230 adapted for leading a user's finger to grasp the traction element 210 at a predetermined location.

The traction element 210 is preferably overmolded onto the head section 208. The traction element 210 may be formed from a molded polymeric material whereas the first surface 202 of the head section 208 is formed from a textile or generally understood as a loop material, indicated as a material in which a series of hooks may engage, or a hook material. The first surface 202 can be formed from any type of flexible material, textile or polymeric, and is not limited to loop material. By being overmolded, the traction element 210 interlocks with the first surface 202, thereby removing the necessity of gluing or using other means to secure the traction element 210 to the first surface 202, although other means for securing the traction element 210 to the first surface 202 are not eliminated from use according to the disclosure. The traction element 210 is arranged so as to be sufficiently pliable to yield to bending of the head section 208, so as not to inhibit flexibility of the attachment 200.

Unlike in conventional alligator attachments having first and second sections with fastener material, such as hook material, adapted to clamp onto a strap surface having loop material, the attachment 200 consists of a single section comprising the elongate section and the head section 206, 208. The traction element 210 is arranged with the spacing 224 from the profile 226 to not reach all the way to the border or periphery of the head section 208. This prevents the head section 208 of the attachment from lifting up from a substrate upon which the second surface 204 is secured, such as a strap when the strap is bent. This arrangement also allows for a more solid connection of a hook-and-loop engagement or fastener system, and allows the traction element 210 to exhibit more flexibility than conventional traction elements that extend to or wrap about a periphery of a head section.

Due to the ergonomic form of the traction element 210, less material can be used, which in turn reduces stiffness while offering a user improved handling of the traction element 210. By using less material and a reduced footprint over the head section 208, the head section 208 is further prevented from lifting up from the surface that it engages. To aid the user, the traction element 210 may be colored differently from the first surface 202 to provide for contrast.

The interchangeable attachment system embodiments of the disclosure advantageously provide an improved attachment between components, the attachment being more cost-effective and intuitive for users by providing interchangeable attachment interfaces suitable for use with different components and providing a reliable and robust attachment to each other. The interchangeable attachment system embodiments of the disclosure thus improve compliant use and reduce costs of manufacturing by mitigating the need to provide component-specific attachment interfaces not only for each component but also for each type of attachment between a limitless number of different components that may be used in a device, such as an orthopedic, prosthetic, or medical device.

It is to be understood that not necessarily all objects or advantages may be achieved under any embodiment of the disclosure. Those skilled in the art will recognize that an interchangeable attachment system may be embodied or carried out in a manner that achieves or optimizes one advantage or group of advantages as taught herein without achieving other objects or advantages as taught or suggested herein.

The skilled artisan will recognize the interchangeability of various disclosed features. Besides the variations described herein, other known equivalents for each feature can be mixed and matched by one of ordinary skill in this art to build and use an attachment system under principles of the present disclosure. It will be understood by the skilled artisan that the features described herein may be adapted to other methods and types of attachment systems and devices.

Although this disclosure describes certain exemplary embodiments and examples of an attachment system, it will be understood by those skilled in the art that the present disclosure extends beyond the specifically disclosed attachment systems to other alternative embodiments and/or uses of the disclosure and obvious modifications and equivalents thereof, including other types and components of various devices, including orthopedic, prosthetic, medical, and otherwise. It is intended that the present disclosure should not be limited by the disclosed embodiments described above and may be extended to other applications that may employ the features described herein.

The invention claimed is:

1. An attachment device defining first and second surfaces, and further defining first and second ends to a length of the attachment device, the attachment device comprising:
   an elongate section having first and second portions defined along the length of the attachment device, the second portion defining the second end of the attachment device;
   a head section extending from the first portion of the elongate section, the head section defining the first end of the attachment device;
   a flap having a first end stitched to and extending from the second portion of the elongate section at a junction along the elongate section, the flap having a first surface and a second surface opposite the first surface, the flap having a second end coextensive with the second end of the attachment device and the second portion of the elongate section;
   a traction element protruding from the first surface and disposed about and within a periphery of the head section along the first surface, the traction element forming a raised profile extending outwardly from the first surface;
   wherein the traction element is formed from a polymeric material, and the head section, the flap and the elongate section are formed from a textile;
   wherein a connection between the traction element and the head section consists of the polymeric material of the traction element interlocking with the textile forming the first surface of the head section.

2. The attachment device of claim 1, wherein the head section has a profile including a rounded portion extending from a first side edge of the elongate section to a tip and a sloped edge extending from the tip to a second side edge of the elongate section, the second side edge being opposite the first side edge, the tip forming a longest extent of the first end of the attachment device.

3. The attachment device of claim 2, wherein the traction element corresponds to the profile of the head section with first and second ends of the traction element on opposed sides of the head section.

4. The attachment device of claim 2, wherein the traction element is spaced away by a predetermined distance from the profile of the head section.

5. The attachment device of claim 1, wherein the traction element defines a different color from a color of the first surface of the head section.

6. The attachment device of claim 1, wherein the second surface extends continuously without interruption across an entirety of the head section and the elongate section between the first and second ends of the attachment device, the second surface extending along an entirety of the length of the attachment device.

7. The attachment device of claim 6, wherein the first surface extends continuously across the head section and the elongate section, the second surface terminating at the junction whereat the flap extends from the elongate section.

8. The attachment device of claim 1, wherein the elongate section is coextensive with the flap at the second end of the attachment device.

9. The attachment device of claim 1, wherein the elongate section and the flap define a same width and extend parallel to one another.

10. The attachment device of claim 1, wherein the elongate section and the flap define hook elements on opposite surfaces to one another from the junction to the second end of the attachment device.

11. The attachment device of claim 1, wherein the elongate section and the head section are flexible and the traction element is rigid relative to the elongate section and the head section.

12. The attachment device of claim 1, wherein the traction element defines first and second slopes leading to the raised profile.

13. The attachment device of claim 12, wherein the raised profile forms a rounded depression oriented toward the first end of the attachment device and arranged for leading a finger to grasp the traction element at a predetermined location, the traction element having first and second ends extending closer to the junction than the rounded depression.

14. The attachment device of claim 1, wherein the traction element is arranged as being pliable and capable of bending along with the head section, the traction element being more rigid than the head section.

15. An attachment device defining first and second surfaces, and further defining first and second ends to a length of the attachment device, the attachment device comprising:
   an elongate section having first and second portions defined along the length of the attachment device, the second portion defining the second end of the attachment device;
   a head section extending from the first portion of the elongate section, the head section defining the first end of the attachment device;
   a flap connected to and extending from the second portion of the elongate section at a junction along the elongate section, the flap having a first surface and a second surface opposite the first surface, the flap having a second end coextensive with the second end of the attachment device and the second portion of the elongate section;

a traction element protruding from the first surface of the attachment device and disposed about and within a periphery of the head section along the first surface, the traction element forming a raised profile extending outwardly from the first surface;

wherein a first material extends along a length of the first surface of the attachment device, the first surface extending along both the head section and the elongate section to the junction, the first material extending along the first surface of the flap;

wherein a second material extends along a length of the second surface of the attachment device, the second surface extending along the length defined between the first and second ends of the attachment device along the head section and the elongate section;

wherein the traction element is formed from a polymeric material, and the head section, the flap, and the elongate section are formed from a textile;

wherein a connection between the traction element and the head section consists of the polymeric material of the traction element interlocking with the textile forming the first surface of the head section;

wherein the raised profile forms a depression arranged for leading a finger to grasp the traction element at a predetermined location.

16. An attachment device defining first and second surfaces, and further defining first and second ends to a length of the attachment device, the attachment device comprising:

an elongate section having first and second portions defined along the length of the attachment device, the second portion defining the second end of the attachment device;

a head section extending from the first portion of the elongate section, the head section defining the first end of the attachment device;

a traction element protruding from the first surface of the attachment device and disposed about and within a periphery of the head section along the first surface, the traction element forming a raised profile extending outwardly from the first surface;

wherein the head section has a profile forming a tip;

wherein the traction element corresponds to the profile of the head section with first and second ends of the traction element on opposed side edges of the head section;

wherein the traction element is spaced away by a predetermined distance from the profile of the head section;

wherein the traction element defines a different color from a color of the first surface of the head section;

wherein the traction element is formed from a polymeric material, and the head section and the elongate section are formed from a textile;

wherein the traction element is arranged as being pliable and capable of bending along with the head section, the traction element being more rigid than the head section;

wherein a connection between the traction element and the head section consists of the polymeric material of the traction element interlocking with the textile forming the first surface of the head section.

\* \* \* \* \*